US005773527A

United States Patent [19]

Tomalia et al.

[11] Patent Number: 5,773,527
[45] Date of Patent: Jun. 30, 1998

[54] NON-CROSSLINKED, POLYBRANCHED POLYMERS

[75] Inventors: Donald A. Tomalia; David M. Hedstrand, both of Midland; Rui Yin, Mount Pleasant, all of Mich.

[73] Assignee: Dendritech, Inc., Midland, Mich.

[21] Appl. No.: 376,100

[22] Filed: Jan. 20, 1995

Related U.S. Application Data

[63] Continuation-in-part of Ser. No. 4,849, Jan. 19, 1993, abandoned, which is a continuation-in-part of Ser. No. 739,167, Aug. 1, 1991, abandoned, which is a continuation-in-part of Ser. No. 573,362, Aug. 27, 1990, abandoned.

[51] Int. Cl.$^6$ .................................................. C08G 73/04
[52] U.S. Cl. .......................... 525/417; 525/374; 525/410; 525/411; 525/412; 525/417; 528/363; 528/397; 528/403; 528/405
[58] Field of Search ........................... 575/374; 528/397, 528/363

[56] References Cited

U.S. PATENT DOCUMENTS

| | | | |
|---|---|---|---|
| 4,261,925 | 4/1981 | Tomalia et al. | 564/94 |
| 4,435,548 | 3/1984 | Tomalia et al. | 525/451 |
| 4,507,466 | 3/1985 | Tomalia et al. | 528/332 |
| 4,544,724 | 10/1985 | Sogah et al. | 526/279 |
| 4,558,120 | 12/1985 | Tomalia et al. | 528/363 |
| 4,568,737 | 2/1986 | Tomalia et al. | 528/332 |
| 4,587,329 | 5/1986 | Tomalia et al. | 528/363 |
| 4,599,400 | 7/1986 | Tomalia et al. | 528/405 |
| 4,631,337 | 12/1986 | Tomalia et al. | 528/391 |
| 4,690,985 | 9/1987 | Tomalia et al. | 525/419 |
| 4,694,064 | 9/1987 | Tomalia et al. | 528/332 |
| 4,713,975 | 12/1987 | Tomalia et al. | 73/865.8 |
| 4,737,550 | 4/1988 | Tomalia | 525/418 |
| 4,758,635 | 7/1988 | Wilson et al. | 525/418 |
| 4,847,328 | 7/1989 | Hutchins et al. | 525/107 |
| 4,851,477 | 7/1989 | Hutchins et al. | 525/123 |
| 4,855,403 | 8/1989 | Meschke et al. | 528/419 |
| 4,857,218 | 8/1989 | Meschke et al. | 252/49.3 |
| 4,857,599 | 8/1989 | Tomalia et al. | 525/259 |
| 4,857,615 | 8/1989 | Bronn et al. | 526/173 |
| 4,857,618 | 8/1989 | Silver et al. | 526/240 |
| 4,871,779 | 10/1989 | Killat et al. | 521/28 |
| 4,906,691 | 3/1990 | Joseph et al. | 525/99 |
| 4,910,268 | 3/1990 | Kobayashi | 525/411 |
| 4,946,824 | 8/1990 | Meschke et al. | 503/216 |
| 5,041,516 | 8/1991 | Frechet et al. | 529/44 |
| 5,124,246 | 6/1992 | Urdea et al. | 435/6 |
| 5,153,273 | 10/1992 | Kobayashi | 525/412 |
| 5,175,270 | 12/1992 | Nilsen et al. | 536/27 |

FOREIGN PATENT DOCUMENTS 9314147  7/1993  WIPO .

OTHER PUBLICATIONS

Nucleic Acids Research, vol. 17, No. 17, Thomas Horn et al., Forks and combs and DNA: the synthesis of branched oligodeoxy–ribonucleotides, Dec. 1989.
Compressed Air Magazine, Jun. 1992, pp. 12–17.
The Scientist, Research, Oct. 28, 1991, p. 16.
D.A. Tomalia, A.M. Naylor, W.A. Goddard, III, Angewandte Chemie, 29/2, pp. 138–175. Feb. 1990.
*Encyclopedia of Polymer Science & Engineering*, vol. 1, pp. 689–690, 695, 704–707 & 725 (1985).
I.M. Kosheleva, P.A. Gemitski, A. I. Chmarin, L.M. Kilesova, D.S. Zhrk. and V.A. Korgin, IZV. Acad. Nauk SSSR Ser. Khim. 8, 1636 (1971).

*Primary Examiner*—Fred Zitomer
*Attorney, Agent, or Firm*—Price, Heneveld, Cooper, Dewitt & Litton

[57] ABSTRACT

This invention discloses non-crosslinked, poly-branched polymers having a comb-burst configuration and a process for preparing such polymers.

28 Claims, 3 Drawing Sheets

NON-CROSSLINKED, POLYBRANCHED POLYMERS

This application is a continuation-in-part application of application Ser. No. 08/004,849, filed on Jan. 19, 1993, now abandoned, which is a continuation-in-part of application Ser. No. 07/739,167 filed Aug. 1, 1991, now abandoned, which is a continuation-in-part of application Ser. No. 07/573,362, filed Aug. 27, 1990, now abandoned.

BACKGROUND OF THE INVENTION

This invention deals with non-crosslinked, poly-branched polymers having a comb-burst configuration and a process for preparing such polymers.

Macromolecular organic compounds having novel structures have been investigated for many years as academic curiosities and very little attention has been paid to their use in industrial applications. Since the early 1980's, there has been a renewed interest in the study and development of such macromolecular materials in order to control their critical molecular design parameters, for example, size, shape, surface chemistry, flexibility and topology, for use in industrial applications. These materials have found such diverse uses as demulsifiers for oil-in-water emulsions, as wet strength agents in the manufacture of paper, as agents for modifying viscosities in aqueous formulations such as paints and as submicron size calibrators. Certain biological uses have also been suggested for these materials.

Structurally, polymers are classified as either linear or branched wherein the term "branched" generally means that the individual molecular units of the branches are discrete from the polymer backbone, yet may have the same chemical constitution as the polymer backbone. Thus, regularly repeating side groups which are inherent in the monomeric structure and are of different chemical constitution than the polymer backbone are not considered as "branches", that is, for example, the methyl groups pendent on a polydimethylsiloxane chain are not considered to be branches of that polymer.

In U.S. Pat. No. 4,507,466, issued Mar. 26, 1985, the patentees therein described the preparation of polymers having "branching" in the following manner.

"To produce a branched polymer, it is necessary to employ an initiator, a monomer, or both that possess at least three moieties that function in the polymerization reaction. Such monomer or initiators are often called polyfunctional. The simplest branched polymers are the chain branched polymers wherein a linear backbone bears one or more essentially linear pendant groups. This simple form of branching, often called comb branching, may be regular wherein the branches are uniformly and regularly distributed on the polymer backbone or irregular wherein the branches are distributed in non-uniform or random fashion on the polymer backbone." "An example of regular comb branching is a comb branched polystyrene as described by T. Altores et al. in J. Polymer Sci., Part A, Vol. 3 4131–4151 (1965) and an example of irregular comb branching is illustrated by graft copolymers as described by Sorenson et al. in "Preparative Methods of Polymer Chemistry", 2nd Ed., Interscience Publishers, 213–214 (1968).

Another type of branching is exemplified by crosslinked or network polymers wherein the polymer chains are connected via tetravalent compounds, e.g., polystyrene molecules bridged or cross-linked with divinylbenzene. In this type of branching, many of the individual branches are not linear, in that, each branch may itself contain groups pendant from a linear chain. More importantly in network branching, each polymer macromolecule (backbone) is cross-linked at two or more sites to other polymer macromolecules. Also the chemical constitution of the cross-linkages may vary from that of the polymer macromolecules. In this so-called cross-linked or network branched polymer, the various branches or cross-linkages may be structurally similar (called regular cross-linked) or they may be structurally dissimilar (called irregularly cross-linked). An example of regular cross-linked polymers is a ladder-type poly(phenylsilsesquinone) [sic] {poly(phenylsilsesquioxane)}."

Sogah, et al., in the background of U.S. Pat. No. 4,544,724, issued Oct. 1, 1985, discusses some of these types of polymers and gives a short review of the many publications and disclosures regarding them.

One of the inventors herein, Donald A. Tomalia, and many of his co-workers have been working in this field for several years and have issued many patents which disclose various non-crosslinked, macromolecular branched assemblies.

For example, U.S. Pat. No. 4,435,548, issued Mar. 6, 1984 discusses branched polyamidoamines; U.S. Pat. No. 4,507,466, issued Mar. 26, 1985, U.S. Pat. No. 4,558,120, issued Dec. 10, 1985, U.S. Pat. No. 4,568,737, issued Feb. 4, 1986, U.S. Pat. No. 4,587,329, issued May 6, 1986, U.S. Pat. No. 4,713,975, issued Dec. 22, 1987, U.S. Pat. No. 4,871,779, issued Oct. 3, 1989, and U.S. Pat. No. 4,631,337, issued Dec. 23, 1986, discuss the preparation and use of dense star polymers, and U.S. Pat. No. 4,737,550, issued Apr. 12, 1988 and U.S. Pat. No. 4,857,599, issued Aug. 15, 1989, discuss bridged and other modified dense star polymers.

Also, other structural configurations of macromolecular materials that have been disclosed include star/comb-branched polymers, such disclosure being found in U.S. Pat. No. 4,599,400, issued Jul. 8, 1986 and U.S. Pat. No. 4,690,985, issued Sep. 1, 1987, and finally, rod-shaped dendrimer polymers are disclosed in U.S. Pat. No. 4,694,064, issued Sep. 15, 1987.

The polyamidoamines referred to supra are also disclosed in U.S. Pat. No. 4,758,635, issued Jul. 19, 1988 to Wilson et al.

Hutchins, et al, in U.S. Pat. No. 4,847,328, issued Jul. 11, 1989 and U.S. Pat. No. 4,851,477, issued Jul. 25, 1989, deal with hybrid acrylic-condensation star polymers and Joseph et al in U.S. Pat. No. 4,857,615, issued Aug. 15, 1989, U.S. Pat. No. 4,857,618, issued Aug. 15, 1989, and U.S. Pat. No. 4,906,691, issued Mar. 6, 1990, deal with condensed phase polymers which are linear polymers having regularly, or irregularly, spaced polymeric branches, essentially on the order of a comb structure macromolecule.

An excellent presentation of the structures and chemistries of many such macromoleculer branched assemblies can be found in Tomalia, D. A., Naylor, A. M., and Goddard, W. A. III, Angewandte Chemie, 29/2 (1990), pages 138 to 175.

However, none of the disclosures of the prior art deal with the novel polymers of the instant invention which are non-crosslinked, poly-branched polymers. For simplicity sake, the polymers of the instant invention can be generally characterized as multiple polymeric branches on multiple polymeric branches.

2 is first grafting and first branching and generation 0;

3 is second grafting and second branching and generation 1;

4 is third grafting and third branching and generation 2;

5 is fourth grafting and fourth branching and generation 3;

6 is $(i+1)^{th}$ grafting and $(i+1)^{th}$ branching and generation i, and 7 is $(i+2)^{th}$ and all iterative grafting and $(i+2)^{th}$ and all interative branching, and generation (i+1) and all subsequent generations.

Figure 2:
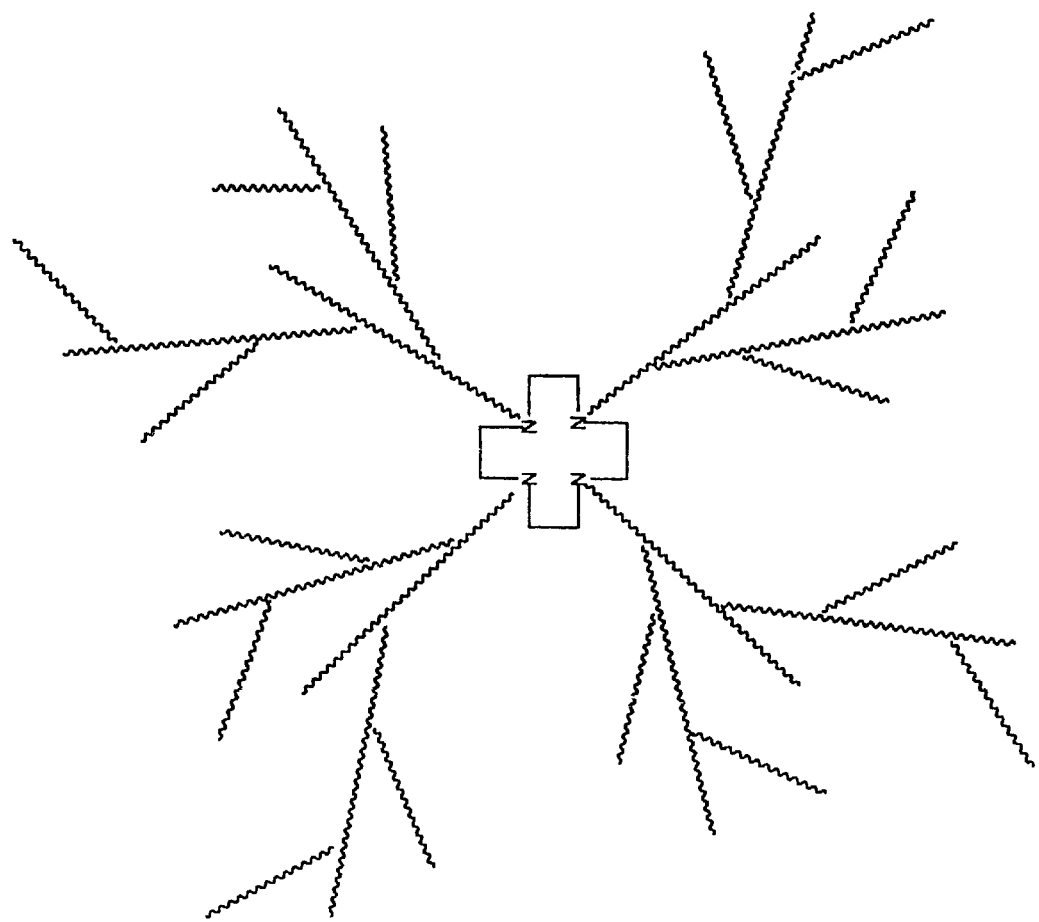
Figure 2:
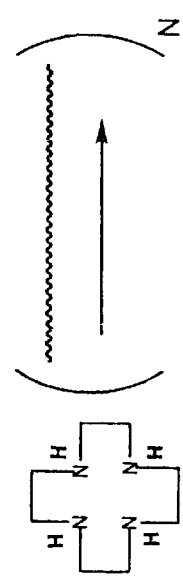
Figure 3:
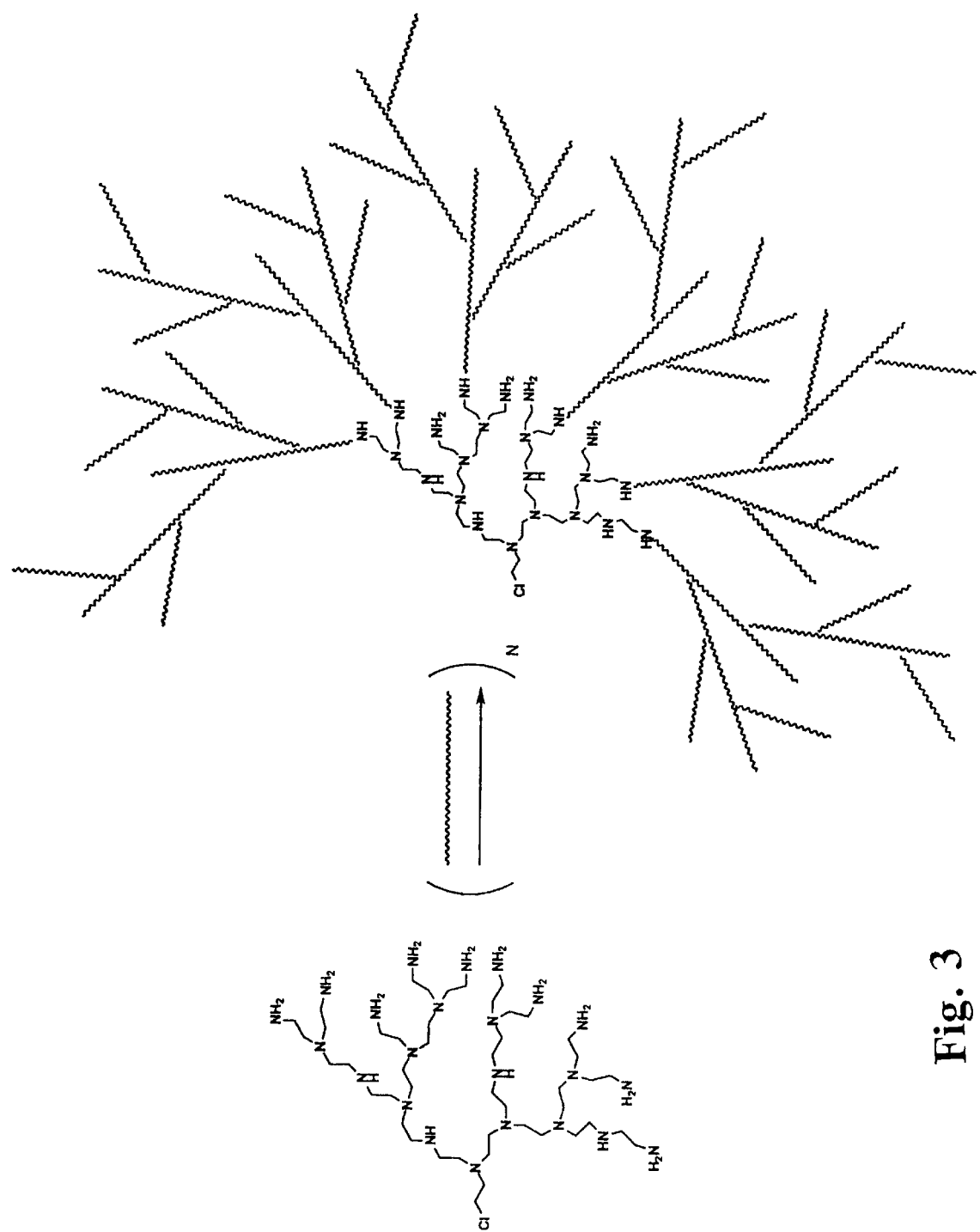

FIG. 2 illustrates the grafting of oligomer branches to cyclen, and the subsequent grafting of branches upon branches; and FIG. 3 shows the grafting of oligomer branches onto a polyethyleneamine dendrimer core, and the subsequent grafting of branches upon branches.

THE INVENTION

Benefits and other perceived advantages are achieved in accord with the present invention which comprises novel non-crosslinked, poly-branched polymers, and methods for manufacturing such polymers. In its broadest scope, this invention deals with poly-branched polymers having at least one branch referred to herein as a "core branch" emanating from a core molecule, said branch being essentially linear, and having at least one end chemically coupled to the core molecule, with the other end of the branch terminating in a group from a molecule used to initiate the reaction by which the branch was prepared, and at least one second branch which is branched from the core branch, said second branch, or branches, being essentially linear, and having at least one end chemically coupled to the core branch, with the other end of the branch terminating in a group selected from a molecule used to prepare the second branch polymer, which when subjected to iterative polymer grafting steps (i.e. generations, which will be delineated further herein), form three-dimensional organizations of ordered organic molecules. These polymers are hereinafter referred to as "comb-burst" structures in that they are prepared from comb-like core molecules, but after subsequent grafting of additional branches pursuant to the processes of this invention, tend to have the appearance in two dimensions of a woven wire fence, which when viewed in three dimensions gives a topology having a starburst-like appearance. Hence, "comb-burst".

This invention therefore comprises compositions of matter comprising non-crosslinked poly-branched polymers having the general formula

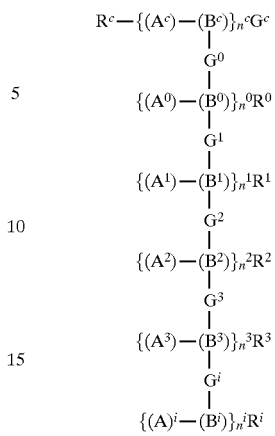

wherein $R^c$ is a non-reactive end group and each $R^o$, $R^1$, $R^2$, $R^3$, and $R^i$ is selected from initiators selected from a group consisting of free radical initiators, cationic initiators, anionic initiators, coordination polymerization initiators and group transfer initiators; (i) represents repetitive linear polymers having the unit formula $\{(A^i)\text{--}(B^i)\}$; $A^c$, $A^o$, $A^1$, $A^2$, $A^3$, and $A^i$ are non-reactive comonomers or, oligomers or polymers formed from a polymerizable monomer, said oligomers or polymers being capable of withstanding the conditions required for preparation of a graft polymer; $B^c$, $B^o$, $B^1$, $B^2$, $B^3$, and $B^i$ are protected or unprotected reactive nucleophilic or electrophilic monomers or, oligomers or polymers formed from a polymerizable monomer, said oligomers or polymers being capable of withstanding the conditions required for preparation of a graft polymer; G is a terminating group or a grafting component and has a value of at least 1; $n^c$ is the degree of polymerization of a core initiator; $n^o$ is the degree of polymerization of a first comb branch; $n^1$ is the degree of polymerization of a first generation comb-burst branch; $n^2$ is the degree of polymerization of a second generation comb-burst branch; $n^3$ is the degree of polymerization of a third generation comb-burst branch, $n^i$ is the degree of polymerization of the $i^{th}$ generation comb-burst polymer having at least one branch point; wherein $n^i \geq 2$ for the case where i=c, $^o$, and 1, and $n^i \geq 2$ if $n^{i+1}$ is > zero, the largest i for which $n^i$ does not equal zero is the total generation level of the polymer wherein the superscripts c, $^o$, 1, 2, 3, and i designate comb-burst generation level; the unit ratio of A units to B units in any $\{(A)\text{--}(B)\}$ segment of the polymer is 0 to 1:100 to 1.

This invention also includes a composition of matter comprising non-crosslinked poly-branched polymers having the general formula

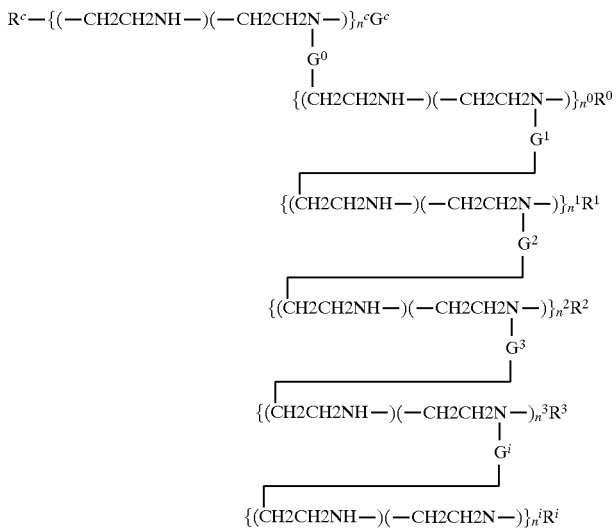

wherein $R^c$ is a non-reactive end group and each $R^o$, $R^1$, $R^2$ $R^3$, and $R^i$ is selected from initiators selected from a group consisting of free radical initiators, cationic initiators, anionic initiators, coordination polymerization initiators and group transfer initiators; (i) represents repetitive linear polymers having the unit formula $\{(-CH2CH2NH-)(-CH2CH2N-)\}$; G is a terminating group or a grafting component and has a value of zero or greater; $n^c$ is the degree of polymerization of a core initiator; $n^o$ is the degree of polymerization of a first comb branch; $n^1$ is the degree of polymerization of a first generation comb-burst branch; $n^2$ is the degree of polymerization of a second generation comb-burst branch; $n^3$ is the degree of polymerization of a third generation comb-burst branch, $n^i$ is the degree of polymerization of the $i^{th}$ generation comb-burst polymer having at least one branch point; wherein $n^i+1 \geq 2$ for the case where i=c, $^o$, and 1, and $n^i \geq 2$ if $n^{i+1}$ is $\geq$ zero, the largest i for which $n^i$ does not equal zero is the total generation level of the polymer wherein the superscripts c, $^o$, 1, 2, 3, and i designate comb-burst generation level; the unit ratio of (—CH2CH2NH—) units to (—CH2CH2N—) units in any (—CH2CH2NH—)(—CH2CH2N—) segment of the polymer is 0 to 1:100 to 1.

There does not seem to be any limit to the size of the dendrimers except that dictated by practicality and/or stereochemistry of the molecules formed. Preferred for this invention are values wherein the molecular weight of the molecules is less than about 1,000,000 and more preferred are those having molecular weights of 250,000 or less. Especially preferred are those molecules having a molecular weight of 100,000 or less, and most preferred are those molecules having a molecular weight of about 30,000.

Values of $n_c$ can be from 2 to a value in excess of 300, but a preferred range for the value of $n_c$ is from 2 to 300. Further, the value of $n^o$ can have a range of 2 to a value of in excess of 100, but the preferred value is from 2 to 100. In addition, values of $n^1$, $n^2$, and $n^i$ can be in the range of 1 to a value in excess of 100, but the preferred range is from 1 to 100.

As indicated above, each of $R^o$, $R^1$, $R^2$, $R^3$, and $R^i$ in these inventive polymers is selected as a moiety from a radical initiator, a moiety from a cationic initiator, a moiety from an anionic initiator, coordination polymerization initiator, a group transfer initiator. $R^o$–$R^i$ can be for example hydrogen, an alkyl group, Lewis acids, or the like such materials being known in the art.

The $G^i$ group is the grafting component formed by the reaction of the living end, or a derivative of the living end, of the $i^{th}$ generation oligomer with the reactive groups of the (i–1) generation material. Thus, an anionic oligomer may be reacted directly with an electrophilic precursor generation, or it may be terminated by, for example, a halogen such as chlorine, bromine, or iodine, to create an electrophilic end group for grafting to a nucleophilic precursor. Similarly, a cationic oligomer may be reacted directly with a nucleophilic precursor generation, or terminated with, for example, water, hydrogen sulfide, or an amine to give a nucleophilic end group for reaction with an electrophilic precursor. In the case of $G^c$, the "graft" is to a monofunctional molecule, which may be as simple as quenching the active end with a proton or hydroxide, as would be the case with normal termination of ionic oligomers with water, or trapping with a specific molecule in order to introduce a single desired functional group to the molecule. Other telechelic groups suitable for grafting purposes may be found in Goethals, "Telechelic Polymers"; Syn. Appln., CRC Press (1989).

The oligomeric and polymeric segments of these materials can be homopolymers or copolymers, it being understood that the formulae herein represent bonding of the grafting G groups to either segment A, if it is present, or to segment B, and it being further understood that the grafting to any A segment is at the terminal end of the molecule, any other segment A grafting would result in the potential for crosslinking the polymers, which is not part of the invention herein. Also, for purposes of this invention, each A segment can be monomeric or, oligomers or polymers formed from polymerizable monomers, the only condition being that the said monomers, oligomers and polymers must be capable of withstanding the conditions required for preparation of subsequent graft junctures. As illustrated in the formulae, the bond from G to the next generation is indicated by a vertical line about halfway between the A segments and the B segments to illustrate that G can be bonded to either A, if it is present, or to B, which is always present in the molecule.

An example of a G group that fits this description would be a urea formed by the reaction of an isocyanate with an amine group. This is formed by the activation of the amines of a poly(vinyl amine) segment with phosgene to create a polyisocyanate precursor molecule which, then, is reacted with an amine terminated poly(vinyl acetamide). The same G group can be formed by treating the poly(vinyl acetamide)

with phosgene to form the telechelic oligomer with isocyanate end group, followed by reaction with the poly(vinyl amine) precursor molecule.

An example using the A group bonded to the G group would be the use of a copolymer of ethyl oxazoline and ethylene oxide. The hydroxyl group on oxyethylene is the terminal group on the reactive oligomer segment. Activation of the hydroxyl group with phosgene gives a chloroformate which is reacted with the amine of a poly(ethyleneimine) segment on the precursor generation to form a urethane. Thus, the A group of the reactive oligomer is the "unreactive" oxyethylene and the B group is the masked iminoethylene, N-propionyl iminoethylene.

The range of possible G groups is limited only by the types of coupling reactions that are possible. In addition to ureas and urethanes, imide, thiourea, thiocarbamate, and anhydride linkages are readily available from similar reagents. Precursor molecules containing olefins that result from polymerization or copolymerization of butadiene or ring opening metathesis polymerization of cyclic olefins can be activated by halogenation for subsequent reaction with a nucleophilic end group, or reacted directly with mercaptans via radical addition, or be coupled with a silane end group via catalyzed hydrosilylation methods. Ether and ester linkages can be derived from hydroxyl groups on either the precursor molecule or the reactive oligomer end group.

Segments of A include for example, —CH$_2$CH$_2$—, —CH$_2$CH=CHCH$_2$—, —CH$_2$C(CH$_3$)$_2$—, —CH$_2$CH(CN)—,

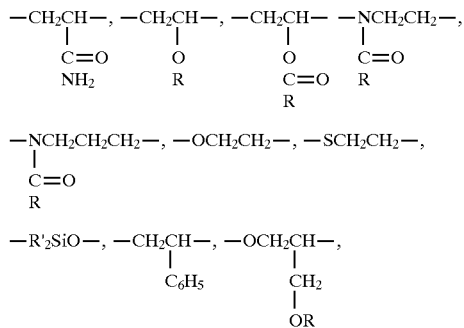

wherein R' is an alkyl group of 1 to 4 carbon atoms, aryls, arylalkyl, hydrogen, or carboalkoxy and R is an alkyl group of 1 to 4 carbon atoms, aryls, or hydrogen;

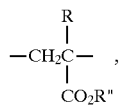

wherein R has the same meaning as set forth above, and wherein R" can be an alkyl group of 1 to 4 carbon atoms.

Preferred as A segments are —CH$_2$CH$_2$—,

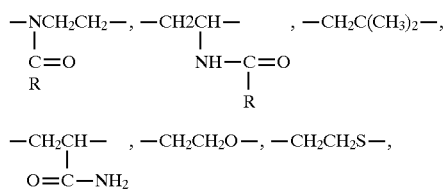

-continued

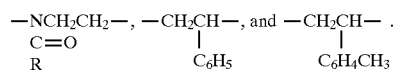

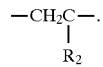

Most preferred are the A segments

—NCH$_2$CH$_2$—, —CH$_2$CH—, and —CH$_2$CH— .
   |                    |                  |
   C=O               C$_6$H$_5$         C$_6$H$_4$CH$_3$
   |
   R Examples of the B segment can be monomeric, or oligomers or polymers formed from polymerizable monomers, wherein said monomers, oligomers and polymers must be capable of withstanding the conditions required for preparation of a graft polymer and further, the B segments must contain at least one unit which is nucleophilic or electrophilic in character.

The groups B contain the reactive sites to which the oligomers may be grafted. In many cases, these groups may need to be present in latent or masked form if they would otherwise be incompatible with the oligomerization process. For example, polymerization of ethyleneimine leads to highly branched polyethyleneimine oligomers which are not useful for this invention because the secondary amines formed are also reactive under the polymerization conditions. Oxazoline polymerization leads to linear polyethyleneimine in a protected form, and the secondary amines can be unmasked for grafting by hydrolysis. For alkylene oxide oligomerizations, hydroxyl groups intended for use as future graft sites would need to be masked as, for example, an ether to preclude the possibility of forming highly cross-linked gel systems. An example of a latent reactive site would be an alcohol group of a polyol which would require activation by conversion to a halide or sulfonate to allow reaction with anionic oligomer.

Thus, B as a nucleophile can be selected from such groups as

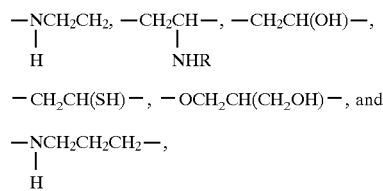

while B as an electrophile can be selected from such groups as

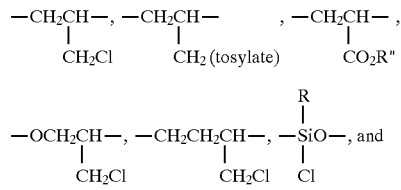

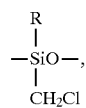

wherein R and R" have the meanings set forth above.

It should be understood that homopolymers consist of only the B segment, while copolymers can be had by combining the B segments with the A segments. Copolymers can also be prepared by using different monomers for the B segment of different generations, for example $B^1$ being different from $B^2$.

The inventors herein contemplate that for purposes of this invention, there must be at least one B segment and therefore the ratio of A segments to B segments ranges from 0 to 1 to 100 to 1.

This invention also comprises a process for preparing non-crosslinked poly-branched polymers having the general formula

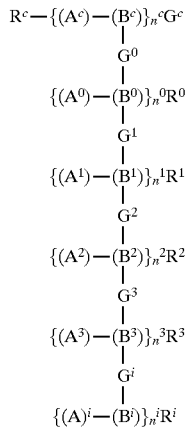

wherein $R^c$ is a non-reactive end group and wherein each $R^o$, $R^1$, $R^2$, $R^3$, and $R^i$ is selected from initiator types selected from a group consisting of free radical initiators, cationic initiators, anionic initiators, coordination polymerization initiators, and group transfer initiators; (i) represents repetitive linear polymers having the unit formula $\{(A^i)\text{--}(B^i)\}$; $A^c, A^o, A^1, A^2, A^3$, and $A^i$ are non-reactive comonomers or, oligomers or polymers formed from a polymerizable monomer, said oligomers or polymers being capable of withstanding the conditions required for preparation of a graft polymer; $B^c, B^o, B^1, B^2, B^3$, and $B^i$ are protected or unprotected reactive nucleophilic or electrophilic monomers or, oligomers or polymers formed from a polymerizable monomer, said oligomers or polymers being capable of withstanding the conditions required for preparation of a graft polymer; G is a terminating group or a grafting component having a value of at least one; $n^c$ is the degree of polymerization of a core initiator; $n^o$ is the degree of polymerization of a first comb branch; $n^1$ is the degree of polymerization of a first generation comb-burst branch; $n^2$ is the degree of polymerization of a second generation comb-burst branch; $n^3$ is the degree of polymerization of a third generation comb-burst branch, $n^i$ is the degree of polymerization of the $i^{th}$ generation comb-burst polymer having at least one branch point; wherein $n^i \geq 2$ for the case where i=c, o, and 1, and $n^i \geq 2$ if $n^{i+1}$ is $\geq$ zero, the largest i for which $n^i$ does not equal zero is the total generation level of the polymer wherein the superscripts c, o, 1, 2, 3, and i designate comb-burst generation level; the unit ratio of A units to B units in any $\{(A)\text{--}(B)\}$ segment of the polymer is 0 to 1:100 to 1, the process comprising (I) forming a linear initiator core having at least one reactive site and having the general formula $R^c\text{---}\{(A^c)\text{--}(B^c)\}_{n^c}\ G^c$; (II) reacting all or part of the sites ($B^c$) of (I) with a reactive polymer having the unit formula $G^o\{(A^o)\text{--}(B^o)\}_{n^o}R^o$ to form multiple branches that contain at least one reactive site on each branch using protection-deprotection reactions to ensure that the unit formula $G^o\{(A^o)\text{--}(B^o)\}_{n^o}R^o$ reacts only with ($B^c$) sites of (I) and that no reactions occur at the reactive sites $B^o$; (III) repeat (II) sequentially to form successive generations of reactive branches to give the desired non-crosslinked poly-branched polymers.

This invention further comprises a process for preparing non-crosslinked poly-branched polymers having the general formula

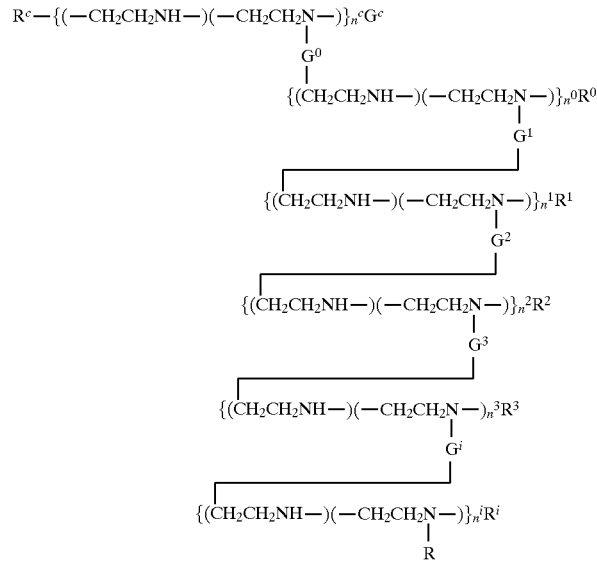

wherein the values of the symbols, superscripts, and subscripts are set forth above.

It should be noted by those skilled in the art that the polymer requires an initiator core (initiator core molecule). This initiator core may or may not be a "living polymer" or "living oligomer", which oligomers and/or polymers are generally known to those skilled in the art. "Living systems" are preferred in order to control polydispersity of the comb-burst dendrimers. Using specific chemistry, the inventors herein can explain this aspect of the invention beginning with reference to "Polymeric Amines And Ammonium Salts", edited by E. J. Goethals, Pergamon Press, (1980), with especial reference to pages 55 et seq. wherein there is taught one method of producing living polymers in a paper entitled "Linear Polyalkylenimines", Saegusa, T. and Kobayashi, S.

Using the example of Saegusa, page 58, one can observe that an initiator such as methyl iodide is first reacted with an oxazoline in the following sequence to give an oligomeric "living oligomer" having, in this case, two protected reactive sites designated as

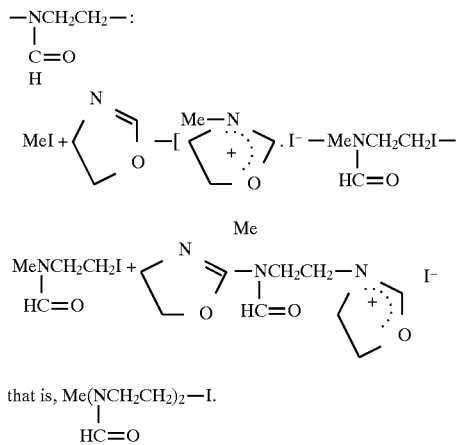

that is, Me(NCH$_2$CH$_2$)$_2$—I.
|
HC=O

Figure 1:
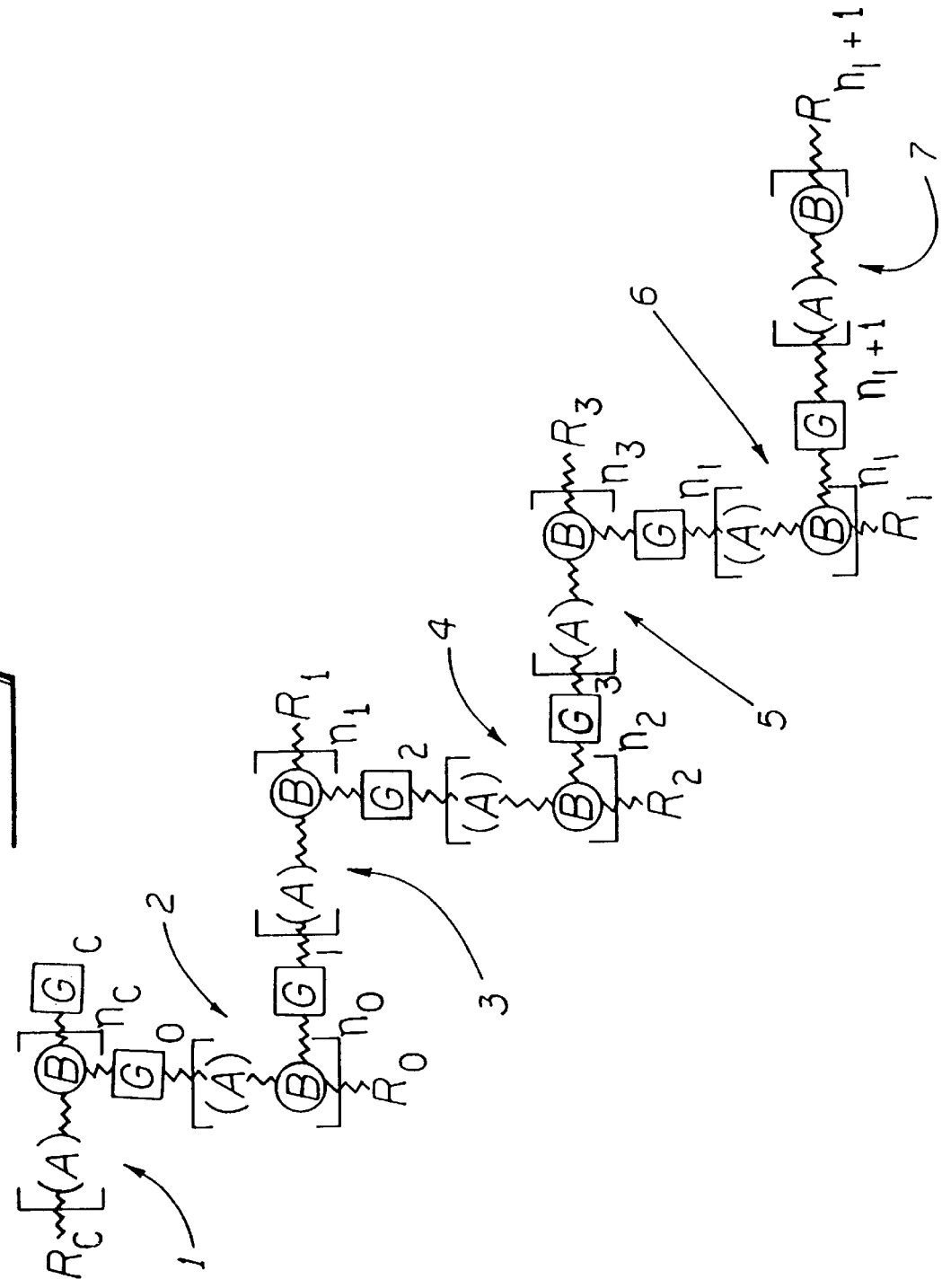
FIG. 1 is a schematic in two dimensions of the polymer configuration of the polymers of the instant invention wherein 1 is the initiator core (initiator core molecule)

With further reference to FIG. 1 of the instant invention, the initiator core in the specific case described just above would be shown in FIG. 1 as $R^c(B^c)_{nc} G^c$; where $R^c$ is methyl and $G^c$ is as described above.

Reaction sequences are then chosen to deprotect the nitrogen groups so that each of the two reactive sites adds a reactant possessing its own, new reactive site, or sites, which introduces multiplicity, to obtain a "dendrimer" —{(A°)--(B°)}$_{n°}$R° of generation 0 (see FIG. 1), wherein "dendrimer" has the same or similar meaning as that used by Tomalia, et. al. in the article referenced supra. As can be observed from the reaction sequence set forth above, this process requires that protection-deprotection strategies are used to ensure that the reactant reacts with all reactive (B$^c$) sites, but does not react any (B°) sites. Protection-deprotection strategies are generally known to those skilled in the art and great detail does not have to be set forth herein. Suffice it to suggest that the living oligomer set forth above has the protective group

on each nitrogen of the oligomer whereupon the oligomer is then hydrolyzed with an acid to give polymeric units having reactive amine groups i.e.

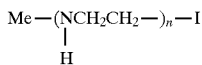

which are then used as the reactive sites to form the next generation, it being understood that the reactive sites of the polymer being grafted to the amine groups are protected before this reaction takes place, and that they too are hydrolyzed after the grafting reaction to give additional reactive sites for the next generation of branching. Additional iterative sequences involving addition of new reactants having reactive sites is then undertaken in order to add branches onto branches to form the poly-branched polymer of this invention until the polymers will not form due to steric hinderence referred to as comb-burst dense packing. The article by Tomalia, et al, referenced supra sets forth such technical terms.

One of the inventive processes used to prepare polymers of this invention relies on the polymerization of 2-ethyl-2-oxazoline. Methyl p-toluenesulfonate has been shown to polymerize oxazolines and the polymerization mechanism has been determined to be cationic, producing a "living polymer". This allows the preparation of polymer samples with well defined molecular weight and low polydispersity. The end of the growing polymer chain contains an oxazolinium ion as disclosed above, that can be trapped by a variety of nucleophiles. To graft the living poly(2-ethyl-2-oxazoline) chains, they are terminated with the secondary amine groups contained on linear poly(ethyleneimine) (LPEI). After grafting onto the linear poly(ethyleneimine) has been accomplished, hydrolysis of the poly(2-ethyl-2-oxazoline) grafts will generate poly(ethyleneimine) branches. This allows further living poly(2-ethyl-2-oxazoline) chains to be grafted onto the poly(ethyleneimine) branches. Repetition of the grafting and hydrolysis forms the inventive polymers with the structures shown herein.

FIGS. 2 and 3 and Examples 31 and 32 below illustrate branching "0" generation branches onto cores comprising ring compounds and dendrimers respectively. In FIG. 2, branches which can be generated in the manner described above are attached to the four nitrogens in the ring compound 1,4,7,10-tetraazacyclododecane (cyclen), much as they are grafted to the nitrogens of a polyethyleneimine core molecule as discussed above. First generation branches are then grafted upon the "0" generation branches, second generation branches are grafted upon the first generation branches, etc. as discussed above.

In FIG. 3, "0" generation branches are grafted to the surface nitrogens of a hyper-terminal-branched or dendrimer core molecule, specifically, a second generation polyethyleneamine. At the generation 2 level (designating the first generation as generation 0), such hyper-terminally-branched molecules are typically referred to as "dendrimers." Hyper-terminal-branched or dendrimer cores can be prepared in various manners known to those skilled in the art including without limitation by the techniques disclosed in U.S. Pat. Nos. 4,507,466 entitled "DENSE STAR POLYMER BRANCHES HAVING CORE, CORE BRANCHES, TERMINAL GROUPS," 4,558,120 entitled "DENSE STAR POLYMER," 4,568,737 entitled "DENSE STAR POLYMERS AND DENDRIMER," 4,587,329 entitled "DENSE STAR POLYMER HAVING TWO-DIMENSIONAL MOLECULAR DIAMETER," 4,631,337 entitled "HYDROLYTICALLY STATE DENSE STAR POLYAMINE," 4,737,550 entitled "BRIDGED DENSE STAR POLYMER," 4,599,400 entitled "STAR/COMB-BRANCH POLYAMIDE," 4,690,985 entitled "STAR/COMB-BRANCHED POLYAMINE," 4,694,064 entitled "ROD-SHAPED DENDRIMER," and 4,857,599 entitled "MODIFIED DENSE STAR POLYMERS." Similarly, any of the dendrimer molecules described in said patents could be used as the hyper-branched dendrimer core to which oligomer branches are grafted in reiterative fashion in accordance with the present invention. One need only develop an appropriate strategy for attaching the oligomer branches to the surface moieties of such hyper-branched cores, and various alternatives will be apparent to those of ordinary skill in the art.

For purposes of clarifying terminology, it should be noted that the hyper-terminal-branched core molecule disclosed in FIG. 3 and in Example 32, and those disclosed in the United States patents discussed above are built by reiterative terminal branching rather than reiterative comb-branching. That is to say, one attaches subsequent generation branches to the terminal moieties of a previous generation, thus limiting the degree of branching to the functionality of the previous generation terminal moiety, which would typically be two or three. In contrast by branching oligomers upon prior generation oligomer branches in accordance with the present invention, one can dramatically increase the degree of branching from generation to generation, and indeed can vary the degree of branching from generation to generation.

EXAMPLE 1

A 250 ml one-necked round-bottomed flask equipped with a magnetic stirring bar and a Dean-Stark trap that was surmounted with a reflux condenser was charged with 2.84 gm (15.3 mmole) of methyl tosylate and 125 ml of toluene. The mixture was heated at reflux and solvent was collected until all water had been removed. At this time, 30.0 gm (303 mmoles) of freshly distilled 2-ethyl-2--oxazoline was added all at once and the mixture was refluxed for approximately 4 hours. During this time, in a separate flask, 1.64 gm (38.1 mmole of repeat units) of linear poly(ethyleneimine) (LPEI) was azeotropically dried with toluene. When the poly(ethyleneimine) was dry it was added to the round-bottomed flask containing the oxazoline oligomer and then allowed to reflux for an additional 3 hours. Any ungrafted living poly(2-ethyl-2--oxazoline) chains were neutralized by the addition of 2.0 ml of water with refluxing for an additional 1 hour. Toluene was removed under reduced pressure to leave a yellowish oily solid that was dissolved in chloroform and precipitated dropwise into diethyl ether. The yellow solid was filtered from solution and dried overnight in a vacuum oven to yield 29.7 gm (94% yield) of grafted poly(2-ethyl-2--oxazoline) (PEOX) as a yellow powder.

EXAMPLE 2

Into a 500 ml one-necked round-bottomed flask was placed 21.6 gm of the oxazoline from example 1 and 350 ml of water. When the polymer had completely dissolved, 35 ml of concentrated sulfuric acid was added. The flask was equipped with a distillation head and the mixture was heated at reflux and distillate was collected until propionic acid could not be detected. Water was added to the distilling pot when the volume was reduced to less than approximately 75 ml. Upon removal of the propionic acid the distillation head was replaced with a reflux condenser surmounted with a pressure equalized addition funnel charged with 5N NaOH. The base was slowly dripped into the reaction mixture maintained at reflux. When the pH of the reaction mixture was approximately 12, heating was discontinued. While standing at room temperature a solid formed at the surface of the aqueous mixture. This solid was removed and placed in a 250 ml round-bottomed flask with 175 ml of toluene. The water was removed from the water-toluene azeotrope by distillation. When water removal was complete, the solid became soluble in the refluxing toluene. The hot toluene solution was poured into a 250 ml round-bottomed flask leaving behind insoluble salts. Toluene was removed under reduced pressure to leave a brownish, waxy solid. The sample was dried for approximately 24 hours under vacuum to give 9.14 gm (97% yield) of polymer sample.

EXAMPLE 3

Using the general method of Example 2, hydrolysis of the graft polymers, was carried out on a separate batch of the graft polymers in the following manner. Five grams (5.0 gm) of the graft copolymer were placed in a 250 ml round-bottomed flask with 100 ml of water and 10 gm of sulfuric acid. The flask was heated with a heating mantle to give a slow distillation of the propionic acid/water azeotrope. The distillation was continued for 2 days, with water being added as necessary to maintain the reaction volume. Approximately 200 ml of distillate was collected over the course of the hydrolysis. The heating was discontinued and 50% NaOH was added slowly to bring the pH to 10. The free polyamine was insoluble in the saturated salt solution, giving a separate phase on top of the aqueous solution. The phases were separated and the polyamine was placed in a 250 ml round-bottomed flask. One hundred fifty ml of toluene was added and a Dean-Stark trap was attached. After reflux overnight (about 16 hours), no more water was being removed and the polyamine had dissolved in the hot toluene. The hot solution was filtered and the solvent was removed from the filtrate using vacuum and agitation to give branched poly(ethyleneimine) weighing 2.2 gm (100% of theory) as an orange oil. The $^{13}$C-NMR spectrum showed a peak for linear poly(ethyleneimine) (49.4 ppm/intensity 8075), residual unhydrolyzed propionamide (9.5 ppm/intensity 156),(26.3 ppm/intensity 180), and primary amine end group (41.7 ppm/intensity 61). No peak for a hydroxy terminal group was observed. While the intensities may not be interpreted as a quantitative measure of the groups present, qualitatively, hydrolysis was 80 to 90% complete and grafting was complete within the limits of detection.

EXAMPLE 4

A 2 liter, 3-necked, round-bottomed, glass flask was used with a shaft driven stirrer, instead of magnetic stirring. The initial loading was: water—250 ml, material prepared essentially by the method of example 3—125 gm, sulfuric acid—150 gm. Additional sulfuric acid, 100 gm was added halfway through the hydrolysis to improve solubility. Internal flask temperature was monitored and a solenoid valve was rigged to add water whenever the temperature rose above 107° C. Thus, constant attention was not necessary and the distillation could be left unattended overnight. The heating mantle was also set to shut off at the same temperature so that the flask would not overheat if the water reservoir ran out of water. After 2 days of continuous distillation, 1.6 liters of distillate was collected. The reaction mixture was neutralized and the polymer phase was separated. The crude polymer was purified by dissolving in hot water (1 liter) and precipitated by slow addition to cold water. After two precipitations, the supernatant solution was neutral to Hydrion$^R$ paper. The resulting hydrated polymer was dehydrated via toluene azeotrope as described above to give LPEI (51 gm 94% yield). The $^{13}$C-NMR spectrum showed LPEI with residual amide carbon intensities 0.5% of the LPEI intensity. Primary amine end group intensity was 0.4% of the LPEI intensity.

EXAMPLE 5

Into a 250 ml round-bottomed glass flask was placed p-toluenesulfonic acid monohydrate (2.0 gm, 11 mmole) and toluene (100 ml). A Dean-Stark trap was attached and the mixture was heated at reflux until water removal was complete. Ethyl oxazoline (10 gm, 100 mmole) was added all at once and the reflux was continued for 2 hours. LPEI (1.0 gm, 23 meq.) was placed in toluene (25 ml) and the mixture was heated to boiling to dissolve the polymer and azeotropically remove trace water in the polymer. The hot LPEI solution was added all at once, to the cloudy oligomer suspension. An orange oil began to precipitate immediately. After 1 hour at reflux, the mixture was cooled and the solvent stripped using vacuum. The residue was dissolved in $CH_2Cl_2$ (40 ml) and precipitated by a slow addition to ether (500 ml). The solid was collected by filtration and dried in a vacuum oven at 40° to 50° C. to give the grafted polymer (12 gm, 92% yield) as a yellow powder. At higher M/I ratios, the oligomerization time had to be increased to allow complete conversion of the ethyl oxazoline. For example, intermediated degree of polymerization runs (M/I=200, olig. time=3 hours. or M/I=400, olig. time=6 hours) had low yields due to incomplete conversion. Increasing the reaction time to 12 hours and 24 hours respectively, gave higher conversions and yields. The highest M/I (1000) run, had an oligomerization time of 36 hours, which was not long enough for complete conversion. This gave a material with actual oligomer dp of 700. The $^{13}$C-NMR spectrum of the poly-branched polymer derived from this material showed a peak for primary amine end groups which was approaching the limits of detection for the signal/noise ratio. No hydroxyl terminal group was detectable.

EXAMPLE 6
Preparation of Morpholine Terminated Linear Polyethyleneimine Having a Degree Of Polymerization (dp) of 20.

A mixture of Methyltosylate (7.46 g, 40 mmol) in 200 ml of toluene was azetroped to dryness with a Dean-Stark trap for about 10 to 15 minutes. To this mixture which had cooled to about 90° C. was added ethyl oxazoline (79.3 g, 800 mmol) and the mixture was refluxed for 18 hours. To this mixture which had been cooled to about 90° C. was added morpholine (14 g, 161 mmol). This mixture was refluxed for 16 hours. This mixture was evaporated of volatiles on a rotary evaporator. This crude mixture was hydrolyzed with 400 ml of 50% $H_2SO_4$ by azeotroping the water-propionic acid mixture with a Dean-Stark trap until about 500 ml were collected or until the pH of the distillate was neutral. This hot mixture was slowly poured into a 50% KOH mixture under an atmosphere of $N_2$. The resulting heterogenous mixture was made homogeneous by heating to reflux. The product floated to the top of this mixture as a clear liquid. This hot mixture was allowed to cool under $N_2$ to room temperature. The solid cake that formed on the surface of this mixture was dissolved in 600 ml of deionized water by heating to reflux, allowed to cool and ultracentrifuged (8000 rpm) for 10 minutes. The clear liquid was decanted and the remaining white solid-water mixture was mixed with toluene. This mixture was azeotroped of water to form a dry toluene-LPEI mixture. The toluene was removed from this mixture by a rotary evaporator followed by high vacuum (0.2 mm Hg) at 80° C. for 2 hours to give 34 g (88% yield) of the title compound.

EXAMPLE 7
Preparation of Comb-Branched PEI Wherein $N_c$ is 20, $N_b$ is 5 and G is zero.

A mixture of Methyl tosylate (MeTOs) (3.7 g 20 mmol) in 50 ml of toluene was azeotroped to dryness with a Dean-Stark trap under nitrogen for 10 minutes. To this mixture cooled to 90° C. was added ethyl oxazoline (10 g, 100 mmol). This mixture was stirred for 10 hours at 90° C. To this mixture was added N-morpholine terminated LPEI (dp of 20) (0.53 g, 0.55 mmol, 11 mmol NH) dissolved in 20 ml of hot (90° C. toluene which had been dried by azeotropic distillation for about 15 minutes. This was immediately followed by the addition of diisopropylethylamine (12 g, 93 mmol, 8 equivalents of amine per NH). This mixture was refluxed for 48 hours. The volatiles were removed from this mixture and the resulting residue dissolved in deionized water. After ultrafiltration (MW>1000), the retentate was refluxed in 400 ml of 50% $H_2SO_4$ for 18 hours. The cooled reaction mixture was made basic to a pH≦14 with KOH to produce a clear colorless liquid that floated to the top of the mixture. Upon cooling the liquid solidified. The solid was removed from the mixture and dissolved in 500 ml of hot deionized water. This mixture was allowed to cool forming a white suspension. This resulting mixture was ultracentrifuged at about 8000 rpm for about 10 minutes. The clear liquid was decanted from the white precipitate. The white precipitate was refluxed with toluene with an attached Dean-Stark trap to dry the product. The toluene mixture was evaporated of volatiles on a rotary evaporator. The remaining volatiles were removed at 0.1 mm Hg at 50° C. to give 1.8 g (70%) of the title compound. A $^{13}$C NMR spectrum of this mixture in $CDCl_3$ indicated a 65% grafting of PEOX onto LPEI as shown by integration of the terminal methyl signals versus the methylene carbon signals.

EXAMPLE 8
Preparation of a Comb-Burst PEI Wherein $N_c$ is 20, $N_b$ is 5, and G is 1.

The compound dendrimer was prepared in the same manner as in example 7 using MeOTs (3.7 g, 20 mmol), 300 ml of toluene, ethyl oxazoline, (10 g, 100 mmol), diisopropylethylamine (12 g, 93 mmol) and comb-branched PEI where $N_c$ is 20, $N_b$ is 10 and G is zero (1.0 g, 23 mmol NH maximum). Ultrafiltration, hydrolysis and drying gave 5.0 g (80% yield) of the title compound. The $^{13}$C NMR spectrum was consistent with the proposed structure.

EXAMPLE 9
Preparation of a Comb-Burst PEI Wherein $N_c$ is 20, $N_b$ is 5 and G is 2.

This example shows the use of the material formed in example 8 which was refluxed with two equivalents of PEOX having a dp of 5 per NH and 11 equivalents of diisopropylethylamine for two days. This mixture was worked up differently than the previous example. The crude PEOX-Comb-Burst PEI was hydrolyzed directly, without ultrafiltration, to give 8.6 g of a Comb-Burst and linear Polyethyleneimine (PEI). This mixture was dissolved in hot deionized water. Upon cooling the product crystallized from the mixture. The mixture was ultracentrifuged at 8000 rpm and the white precipitate was azeotropically dried with toluene to give 4.5 g for a yield of 72%.

EXAMPLE 10
Preparation of a Comb-Burst PEI Wherein $N_c$ is 20, $N_b$ is 5, and G is 3.

The preparation of Comb-Burst PEI where G is 3 incorporated improvements in the grafting step by using two equivalents of PEOX per NH and 26 mmols of diisopropylethylamine per NH. The crude material was hydrolyzed as before and the resulting mixture precipitated from PEI by making basic with KOH. Recrystallization of the cake of product floating on the KOH mixture from deionized water followed by ultracentrifugation at 8000 rpm and azeotropic drying of the white solid with toluene gave 5.6 g for a 90% yield.

EXAMPLE 11
Preparation of a Comb-Burst PEI Wherein $N_c$ is 20, $N_b$ is 5 and G is 4.

The comb-Burst PEI was prepared in a manner similar to the previous example, using two equivalents of PEOX per NH, and 23 equivalents of diisopropylethylamine per NH and refluxing two days. The crude mixture wasn't ultrafiltered but hydrolyzed with $H_2SO_4$, removed from solution by KOH and recrystallized twice from deionized water. Each recrystallization involved dissolving the product in hot water, allowing the mixture to cool to 25° C. and ultracentrifugation at 8000 rpm, 10 minutes. The clear supernatent was decanted from the white solid and the white solid was azeotropically dried with toluene. The isolated yield from the second recrystallization came to 4.9 g for a yield of 78%. The first recrystallization gave 5.5 g, for a yield of 87%.

EXAMPLE 12
Preparation of Comb-Burst PEI Wherein $N_c$ is 20, $N_b$ is 5 and G is 5.

The next generation (G) was prepared at twice the scale of all the other grafting experiments (2.0 g starting material versus 1.0 g of starting material). Only 4 to 5 equivalents of diisopropylethylamine per NH were used along with two equivalents of PEOX per NH and refluxing two days. After evaporating the volatiles the crude mixture was dissolved in deionized water and ultrafiltered using a spiral wound cartridge Amicon S1Y3 (3000 MWCO). Hydrolysis of the retentate gave an 85% yield of the title compound. The ultrafiltration with this membrane was not tried on earlier generations of G=1 to 4.

EXAMPLE 13
Preparation of Comb-Burst PEI Wherein $N_c$ is 20, $N_b$ is 5, and G is 6.

This generation was prepared in a similar manner as before using two equivalents of PEOX per NH, six equivalents of diisopropylethylamine per NH and refluxing two days. The workup again was done by ultrafiltration in deionized water using a spiral wound S1Y3 membrane. The isolated yield of PEOX-Comb-Burst after ultrafiltration came to one-half the amount normally obtained from an 80 to 90% grafting experiment. Hydrolysis of the mixture as before followed by treatment with NaOH and azeotropic drying with toluene gave only a 32% yield of the G=6 product. A repeat of this same experiment except with two recrystallizations in water instead of an ultrafiltration gave a 38% yield of the title compound.

EXAMPLE 14
Preparation of a Comb-Branched PEI Wherein $N_c$ is 20, $N_b$ is 10 and G is zero.

A mixture of MeOTs (7.4 g, 40 mmol) in 100 ml of toluene was azeotroped to dryness with a Dean-Stark trap under nitrogen for 10 to 15 minutes. To this mixture, cooled to about 90° C., was added ethyl oxazoline (39.7 g, 400 mmol). This mixture was refluxed under nitrogen for 18 hours. To this mixture was added N-morpholine terminated LPEI having a dp of 20 (1.0 g, 1.1 mmol, 23 mmol of NH) dissolved in 50 ml of hot (100° C.) toluene which had been dried by azeotropic distillation for 15 minutes. This was immediately followed by the addition of diisopropylethylamine (24 g, 186 mmol, 8 eqivalents amine per NH). This mixture was refluxed for 48 hours. The mixture was cooled, dissolved in methanol and evaporated of volatiles on a rotary evaporator and the resulting mixture was dissolved in deionized water (about 60 ml). This mixture was ultrafiltered using an Amicon spiral wound cartridge S1Y3 with the above volume as a retentate until 12 liters of permeate had been obtained (20 recirculations). This retentate was refluxed in 400 ml of 50% $H_2SO_4$ with a Dean-Stark trap collecting about 400 to 500 ml of distillate (replenishing the equivalent water) until the distillate was neutral to pH paper. This hot mixture was made basic by pouring slowly into a 50% KOH mixture under a blanket of nitrogen. The heterogenous mixture was heated to a homogeneous mixture that produces a liquid that floats to the top of the mixture. Upon cooling the liquid solidified. The solid was removed form the mixture and is solved in 500 ml of hot deionized water. This mixture was allowed to cool forming a white suspension. This resulting mixture was ultracentrifuged at 8000 rpm for about 10 minutes. The clear liquid was decanted from the white precipitate. The white precipitate was refluxed with toluene with an attached Dean-Stark trap to dry the product. The toluene mixture was evaporated of volatiles on a rotary evaporator. The remaining volatiles were removed at 0.1 mm Hg at 50° C. to give 1.8 g (70%) of the title compound. A $^{13}C$ NMR spectrum of this mixture in CDCl, indicated a 65% grafting of PEOX onto LPEI as shown by integration of the terminal methyl signals versus the methylene carbon signals.

EXAMPLE 15
Preparation of a Comb-Branched PEI Wherein $N_c$ is 20, $N_b$ is 10 and G is Zero.

A mixture of morpholine-terminated LPEI having a dp of 20 (1.04 g, 22 mmol), PEOX oligomers having a dp of 10 (47.5 g, 40 mmol) and diisopropylethylamine (20 g, 6 to 7 equivalents per NH) were refluxed under nitrogen obtained from a nitrogen cylinder (constant pressure and no flow) and a Hg bubbler for 48 hours. The volatiles were removed from the mixture and the resulting yellow orange residue was dissolved in 1 liter of deionized water. The mixture was ultrafiltered with an Amicon spiral wound cartridge using 700 ml of retentate and 8.5 liters of permeate to give 24 grams of the PEOX-Comb-Branched PEI copolymer. The material was hydrolyzed with 50% $H_2SO_4$ and the resulting mixture added to an excess of 50% KOH. The cake floating on the KOH was mixed with toluene and azeotropically dried under nitrogen to give 10.1 g (90%) of the Comb-branched PEI dendrimer.

EXAMPLE 16
Preparation of a Comb-Burst PEI Wherein $N_c$ is 20, $N_b$ is 10 and G is One.

The preparation of G=1 of this Comb-Burst PEI series was identical in all respects to the preparation of G=0. The isolated yield of the title compound from 1.1 g of G=0 Comb-branched PEI was 10.5 g (84%). The $^{13}C$ NMR system showed a little more of the carbinol signal at 60.1 ppm than before, plus a signal at 59.46 ppm.

EXAMPLE 17
Preparation of Comb-burst PEI Wherein $N_c$ is 20, $N_b$ is 10 and G is 2.

This material was prepared as described in the previous preparations utilizing an Amicon S1Y10 sprial wound ultrafiltration cartridge (10,000 MWCO) (600 ml retentate/9 liters of permeate). From 1.1 g of Comb-burst PEI wherein G=1, there was obtained 10.8 g (86%) of the title product. The $^{13}C$ NMR spectrum indicated more of the signal at 60.1 ppm than at 59.67 ppm.

EXAMPLE 18
Preparation of a Comb-burst PEI Wherein $N_c$ is 20, $N_b$ is 10 and G is 3.

The material was prepared as described before using an Amicon S1Y10 sprial wound ultrafiltration cartridge (10,000 MWCO) and filtration volumes as described before. From 1.1 g (25 mmol NH) of Comb-burst PEI dendrimer wherein $N_c$ is 20, $N_b$ is 10 and G is 2 there was obtained 10.3 g (82%) of the Comb-burst PEI dendrimer wherein $N_c$ is 20, $N_b$ is 10, and G is 3. The $^{13}$C NMR spectrum of the material again indicated carbinol signals at 60.1 ppm and 57 ppm.

EXAMPLE 19
Preparation of Comb-burst PEI Wherein $N_c$ is 20, $N_b$ is 10 and G is 4.

This material was prepared as described above using an Amicon S1 Y10 spiral wound ultrafiltration cartridge with the volumes indicated above. From 1.1 g (25 mmol NH maximum) of Comb-burst PEI dendrimer wherein $N_c$ is 20, $N_b$ was 10, and G was 3, there was obtained 10.1 g of the title compound. (80% yield).

EXAMPLE 20
Preparation of a Comb-burst PEI Wherein $N_c$ is 20, $N_b$ is 10, and G is 5.

This material was prepared as described above utilizing 1.1 g (25.5 mmol NH) of Comb-burst PEI wherein $N_c$ is 20, $N_b$ is 10 and G is 4, 47.5 g (40 mmol) of PEOX oligomer, and 25 g (8 equivalents of amine per NH) of diisopropylethylamine. Workup as before using an Amicon S1Y10 spiral wound cartridge (700 ml of retentate, and 9 liters of permeate) gave 18 g of the PEOX-Comb-burst copolymer. Hydrolysis with 50% $H_2SO_4$ and treatment with excess NaOH gave a cake of material that floated on the caustic mixture with a lot of trapped NaOH and sodium sulfate salts. The cake was heated in 300 ml of deionized water to boiling and allowed to cool giving a white precipitate. This mixture was ultracentrifuged at 8000 rpm for 10 minutes and the resulting clear liquid was poured from the settled white solid. This white solid was mixed with toluene and dried by azeotropic distillation to give 7.0 g (56%) of the title compound.

EXAMPLE 21
Preparation of a Comb-branched PEI Wherein $N_c$ is 20, $N_b$ is 20 and G is Zero.

A PEOX oligomer having a dp of 20 was prepared from MeOTs (7.5 g, 40 mmol) and ethyl oxazoline 80 g, 800 mmol) by refluxing under tank nitrogen using a Hg bubbler. The LPEI (0.5 g, 0.52 mmol, 10 mmol per NH) in hot toluene was added to the PEOX oligomer followed by diisopropylethylamine (74 g, 574 mmol, 29 mmol per NH). This mixture was refluxed for 72 hours. The volatiles were removed and the resulting residue was dissolved in deionized water. This mixture was ultrafiltered using a S1Y3 cartridge. Workup as before gave 9.8 g of a PEI product (theory 9.1 g). The $^{13}$C NMR spectrum of this material indicated a significant amount of a carbinol signal at 60.2 ppm.

EXAMPLE 22
Preparation of a Comb-Branched PEI polymer Wherein $N_c$ is 20, $N_b$ is 20 and G is Zero In this experiment, two equivalents of PEOX oligomer per NH of the PEI and diisopropylethylamine (30 equivalents per NH of PEI) were refluxed for five days. A very large stir bar was used to get more efficient stirring of the mixture than was obtained in the above experiment. The mixture was stripped of volatiles and the resulting residue dissolved in deionized water. Ultrafiltration of this mixture using the S1Y3 spiral wound cartridge gave no separationas as determined by SEC. The SEC plot indicated two peaks. Upon co-injection with authentic PEOX oligomer having a dp of 20, one of the peaks was enhanced. The ultrafiltration was then carried out on a S1Y10 (10,000 MWCO) spiral wound cartridge. The SEC plot of the retentate was identical to the S1Y3 cartridge retentate.

The ultrafiltration was switched to an Amicon flat stock stirred cell system using a YM10 (10,000 MWCO) cartridge. After 1.5 liters of permeate only a small amount of the presumed PEOX oligomer having a dp of 20 had been ultrafiltered.

The material was then ultrafiltered with the flat stock stirred cell using a YM 30 membrane (30,000 MWCO) (100 ml, retentate; 2000 ml permeate) to give a good separation by SEC. The retentate evaporated to 18 g (42%) of the PEOX-Comb-branched PEI copolymer. This material hydrolyzed to 7.0 g (38%) of the Comb-branched PEI. The $^{13}$C NMR spectrum of the Comb-branched PEI indicated only a minor amount (about 10%) of the carbinol signal at 60.1 ppm relative to the methyl terminated signal at 36.5 ppm.

EXAMPLE 23
Preparation of a Comb-Burst PEI Polymer Wherein $N_c$ is 20, $N_b$ is 20 and G is One.

This material was prepared with two equivalents of PEOX oligomer having a dp of 20 refluxing with diisopropylethylamine for three days. The reaction parameters were to be held constant to permit a reasonable analysis of the chemistry. An analysis of the crude reaction mixture by SEC at 48 hours, 72 hours and 96 hours indicated a progressive increase in molecular weight. Ultrafiltration of the crude material in water with the Amicon flat stock stirred cell using a YM30 (30,000 MWCO) membrane as before (100 ml, retentate; 2000 ml permeate) gave a 74% yield of the PEOX-Comb-burst PEI copolymer. Hydrolysis and treatment with NaOH, recrystallization from water, and azeotropic drying in toluene, gave a 68% yield of the title compound.

EXAMPLE 24
Preparation of a Comb-Branched PEI Polymer Wherein $N_c$ is 20, $N_b$ is 100 and G is Zero.

Further exploration of the PEOX chain length on the grafting efficiency was done. A PEOX having a dp of 100 was prepared (24 hrs at reflux) and refluxed 65 hours with PEI (1 equivalent PEOX per NH) with 11 equivalents of diisopropylethylamine per NH. The mixture was evaporated of volatiles, dissolved in deionized water and ultrafiltered with an S1Y30 (30,000 MWCO) cartridge. Hydrolysis of the retentate and workup gave a 31% yield of a white amorphous powder. Hydrolysis of the permeate gave a white crystalline material, LPEI having a dp of 100.

EXAMPLE 25
Preparation of a Styrene Core Polymer

The styrene core polymer precursor was prepared by polymerization of 20 g (192 mmol) of styrene in benzene (20 ml), initiated by s-butyl lithium (4 mmol). After 4 hours, the reaction was terminated by addition of methanol (1 ml.) Chloromethylation of the product polymer (10 g polystyrene, 60 ml chloromethyl methyl ether, and 1 ml stannic chloride in 500 ml of carbon tetrachloride for 48 hours) gave the chloromethylated core polymer.

EXAMPLE 26
Preparation of a Comb-Branched Polystyrene Wherein G is Zero.

Living polystyrene oligomer was generated by initiation of 20 g of styrene by 4 mmol of s-butyl lithium, as in example 25. After 4 hours at room temperature, 6 mmol of diphenylethylene in 350 ml of tetrahydrofuran was added. The chloromethylated polystyrene core was added portionwise, over 30 minutes, until most of the orange color of the carbanion had disappeared. After an additional 30 minutes, residual carbanions were terminated by the addition of 1 ml of methanol. Evaporation of the solvent and fractionation in toluene/methanol gave an 80% yield of the title compound.

EXAMPLE 27
Preparation of a Comb-Burst Polystyrene Polymer Wherein G is Equal to One.

The product of example 26 was chloromethylated as described in example 25. Grafting was carried out as described in example 26, substituting the chloromethylated-comb-branched material for the linear-chloromethylated-polystyrene core.

EXAMPLE 28
Preparation of a Comb-Burst Polystyrene Polymer Wherein G is 2.

The product of example 27 was chloromethylated as described in example 25. Grafting was carried out as described in example 26, substituting the chloromethylated-comb-burst material for the linear-chloromethylated-polystyrene core.

EXAMPLE 29
Preparation of Rod-Shaped Comb-Burst PEI wherein $N_c$ is 200, $N_b$ is 5 and G is 3.

This material was prepared as described above using N-morpholine terminated PEI as an initiator core. Repeated grafting (4 times) with Methyl Tosylate (3.7 g, 20 mmol) and ethyl oxazoline (10 g, 100 mmol) in 100 ml of toluene, followed by hydrolysis with 150 ml of 50% $H_2SO_4$ gave the dendrimers in a 70 to 80% yields. These products were characterized by $^{13}$C-NMR spectroscopy, titration and electrophoresis and shown to be the titled material.

EXAMPLE 30
Preparation of Spherically-Shaped Comb-Burst PEI wherein $N_c$ is 10, $N_b$ is 100 and G is 3.

This material was prepared in the same manner as the rod-shaped dendrimer using LPEI (dp of 10) as an initiator core. The branches were constructed with PEOX (dp of 100), initiated as shown in the examples above.

EXAMPLE 31
Synthesis of Ring Core Hyper-Combbranched Polymers

AZACROWN™ (1,4,7,10-tetraazacyclododecane, cyclen) was obtained from The Dow Chemical Company, and was further recrystallized from toluene. The purified AZACROWN™ is a white needle-like crystal.

A mixture of methyl tosylate (MeOTs)(0.922 g, 4.95 mmol) in 100 ml of toluene was azeotroped to remove water with a distillation head under Ar for 10 minutes. After cooling to ~90° C., 2-ethyloxazoline (10 ml, 99.06 mmol) was cannulated in and the mixture was allowed to reflux for 5 hours. To this mixture was added a AZACROWN™ core (0.214 g, 4.95 mmol of NH), which was dried by azeotropic distillation from toluene, followed by immediate addition of diisopropylethylamine (i-Pr$_2$NEt)(2–4 eq.). The mixture was refluxed for 1 hour, cooled, and then dissolved in methanol (~100% grafting yield as determined by SEC). After rotary-evaporation of the solvents, the crude product was either purified by ultrafiltration with Amicon spiral wound cartridges S1Y3 (3,000 MWCO), or fractionated by methanol/diethyl ether mixture to remove the unreacted monomers, oligomers, and catalysts. The entire separation process was monitored by size exclusion chromatography (SEC). The purified product was rotary-evaporated and lyophilized to give a ring-branched polyethyloxazoline-polyethyleneimine (PEOX-PEI) polymer as a white powder. The higher generations of the ring core comb-burst polymers can be prepared in a similar manner as described in the linear core case as described above. All the products were analyzed by size exclusion chromatography (SEC), capillary electrophoresis (CE), nuclear magnetic resonance (NMR), and electrospray mass spectroscopy (ES-MS).

EXAMPLE 32
Synthesis of Hyper-Terminally Branched Core Hyper-Combbranched Polymers A mixture of MeOTs (0.39 g, 1.98 mmol) in 100 ml of toluene was azeotroped to remove water with a distillation head under Ar for 10 minutes. After cooling to ~90° C., 2-ethyloxazoline (10 ml, 99.06 mmol) was cannulated in and the mixture was allowed to reflux for 5 hours. To this mixture was added a hyper-branched polyethylene amine core (0.214 g, 4.95 mmol of NH), which was dried by azeotropic distillation from toluene, followed by immediate addition of i-Pr$_2$NEt (large excess). The mixture was refluxed for 3 hours, cooled, and the top toluene solution was decanted off. The remaining viscous oil was redissolved in a small amount of MeOH and reprecipitated out in diethyl ether (Et$_2$O). After the top Et$_2$O solution was decanted, the bottom precipitate was redissolved in methanol (MeOH) and dried over rotary evaporator and high vacuum to give a light yellow polyethyloxazoline-polyethyteneamine (PEOX-PEA) polymer. The higher generations of the hyper-branched core comb-burst polymers can be prepared in a similar manner as described in the linear core case described above. All the products were analyzed by SEC and NMR. Instrumental for Examples 31 and 32.

SEC measurements were performed on a series of Beckman TSK 4000 PW (or POLY-OH, Polymer Laboratory), 3000 PW, and 2000 PW columns using Waters 510 HPLC pump, Thermo Separation Products AS 3000 Autosampler, Wyatt DAWN DSP-F Multi Angle Laser Light Scattering Detector, and Wyatt interferometer refractometer (Optilab 903). $^1$H and $^{13}$C NMR spectra were obtained on Brucker 360 MHz or Varian Unity 300 MHz NMR spectrometer using either CDCl$_3$ or MeOD as solvents. Purity of monomers was checked by GC (HP 5890, He as carrier gas). Ultra filtration was achieved using either an Amicon 3,000 or 10,000 molecular weight cut off (MWCO) membrane. CE was performed on Beckman P/ACE System 2050 (Software System Gold). The polymer MWs were also measured by ES-MS (Finnigan Mat TSQ 700).

What is claimed is:

1. A composition of matter comprising non-crosslinked poly-branched polymers having the general formula

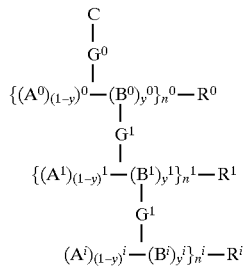

wherein:

C is a core molecule; each {(A)-(B)} branch is a linear polymer or copolymer chain; each R is the residual moiety of an initiator;

A and B are polymerizable monomers or comonomers capable of withstanding the conditions required for branching therefrom or grafting thereto, at least during the polymerization of the {(A)-(B)} linear polymer chain and during its grafting to a prior {(A)-(B)} branch; each G is a grafting component, and the designation

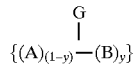

indicates that G can extend from either an (A) unit or a (B) unit; n is the degree of polymerization of the indicated generation comb branches; y is the fraction of B units in the indicated generation branch, and has a value of 0.01 to 1; the superscripts 0, 1 and i designate the comb branch generation level, with i beginning at "2" and continuing for the number of reiterative branch set generations in the polymer; and at least $n^o$ and $n^1$ are $\geq 2$.

2. A composition of matter as claimed in claim 1 wherein each B segment in at least one branch has the unit formula

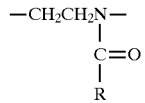

during polymerization of the B segment.

3. A composition of matter as claimed in claim 2 which is a hydrolysis product.

4. A composition of matter as claimed in claim 1 wherein each said A segment in at least one branch has the unit formula

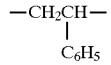

and each said B segment in at least one branch has the unit formula

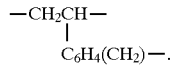

5. The composition of claim 1 in which said polymerizable monomers or comonomers in a given generation of branches are capable of withstanding the conditions required for branching therefrom or grafting thereto by being either protected from or inactive to such branching or grafting at least during said {A--B} polymerization; at least said B monomers or comonomers having been either deprotected or activated subsequent to polymerization and grafting to said core or a prior branch in order to facilitate subsequent grafting thereto or branching therefrom.

6. The composition of claim 5 in which said B monomers or comonomers in a given branch are protected during said polymerization, and are subsequently deprotected by hydrolysis.

7. The composition of claim 5 in which said B monomers or comonomers in a given branch are inactive during said polymerization and are activated by adding a branch or graft reactive group thereto.

8. A composition of matter as claimed in claim 1 in which: A is $(-CH_2CH_2NH-)_x$ and B is

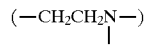

and wherein each of said branches is formed from monomers which leave a protective member on each nitrogen atom in the branch whereby grafting to or branching from said monomer is prevented during polymerization of said branch or during its grafting to a prior branch or to the core, at least some of which are subsequently removed from said branch by a deprotection step performed subsequent to polymerization and grafting of said branch to a prior branch or to said core, to facilitate subsequent grafting to said deprotected branch.

9. A composition of matter as claimed in claim 8 in which said deprotection is effected by hydrolysis.

10. A composition of matter as claimed in claim 8 wherein said protective member on said nitrogen atom is

11. A composition as claimed in claim 8 wherein linear polyethyleneimine is reacted with oxazoline oligomers and is grafted thereby.

12. A composition as claimed in claim 11 wherein the oxazoline oligomer is poly-2-alkyl substituted oxazoline.

13. A composition as claimed in claim 11 wherein the oxazoline oligomer is poly-2-aryl substituted oxazoline.

14. A composition as claimed in claim 13 wherein the grafted polymer is hydrolyzed after grafting.

15. A composition as claimed in claim 12 wherein the grafted polymer is hydrolyzed after grafting.

16. A composition as claimed in claim 11 wherein the grafted polymer is hydrolyzed after grafting.

17. The composition of claim 1 in which said core molecule "C" comprises a ring compound.

18. The composition of claim 17 in which said ring compound is an aza ring compound.

19. The composition of claim 18 in which said core molecule "C" comprises 1,4,7, 10-tetraazacyclododecane.

20. The composition of claim 17 in which said polymerizable monomers or comonomers in a given generation of branches are capable of withstanding the conditions required for branching therefrom or grafting thereto by being either protected from or inactive to such branching or grafting at least during said {A--B} polymerization; at least said B monomers or comonomers having been either deprotected or activated subsequent to polymerization and grafting to said core or a prior branch in order to facilitate subsequent grafting thereto or branching therefrom.

21. A composition of matter as claimed in claim 17 in which:
A is $(-CH_2CH_2NH-)$, and B is

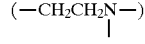

and wherein each of said branches is formed from monomers which leave a protective member on each nitrogen atom in the branch whereby grafting to or branching from said monomer is prevented during polymerization of said branch or during its grafting to a prior branch or to the core, at least some of which are subsequently removed from said branch by a deprotection step performed subsequent to polymerization and grafting of said branch to a prior branch or to said core, to facilitate subsequent grafting to said deprotected branch.

22. The composition of claim 1 in which said core "C" comprises a hyper-branched molecule.

23. The composition of claim 22 in which said hyper-branched core molecule is a dendrimer.

24. The composition of claim 22 in which said polymerizable monomers or comonomers in a given generation of branches are capable of withstanding the conditions required for branching therefrom or grafting thereto by being either protected from or inactive to such branching or grafting at least during said {A--B} polymerization; at least said B monomers or comonomers having been either deprotected or activated subsequent to polymerization and grafting to said core or a prior branch in order to facilitate subsequent grafting thereto or branching therefrom.

25. A composition of matter as claimed in claim 22 in which:

A is (—CH$_2$CH$_2$NH—)$_x$ and B is

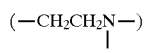

and wherein each of said branches is formed from monomers which leave a protective member on each nitrogen atom in the branch whereby grafting to or branching from said monomer is prevented during polymerization of said branch or during its grafting to a prior branch or to the core, at least some of which are subsequently removed from said branch by a deprotection step performed subsequent to polymerization and grafting of said branch to a prior branch or to said core, to facilitate subsequent grafting to said deprotected branch.

26. The composition of claim 1 in which the degree of branching varies between at least one generation and the next.

27. A composition of matter comprising non-crosslinked poly-branched polymers formed by: (1) forming a first set of branches by initiating the polymerization of a first set of monomers which are either protected against or non-reactive to branching and grafting during said polymerization, each of said branches having a reactive end unit upon completion of said polymerization, said reactive end units being incapable of reacting with each other; (2) grafting said branches to a polymeric core having a plurality of reactive sites capable of reacting with said reactive end groups on said branches; (3) either deprotecting or activating a plurality of monomeric units on each of said branches to create reactive sites; (4) separately forming a second set of branches by repeating step (1) above with a second set of monomers; (5) attaching said second set of branches to said first set of branches by reacting said reactive end groups of said second set of branches with said reactive sites on said first set of branches.

28. The composition of claim 27 which further includes reiterating steps (3), (4) and (5) above to reiteratively add one or more subsequent sets of branches.

* * * * *

UNITED STATES PATENT AND TRADEMARK OFFICE
CERTIFICATE OF CORRECTION

PATENT NO.    : 5,773,527
DATED         : June 30, 1998
INVENTOR(S)   : Donald A. Tomalia, David M. Hedstrand and Rui Yin It is certified that error appears in the above-identified patent and that said Letters Patent is hereby corrected as shown below:

\*Column 1, line 55;

Remove the "quotation mark" before "An".

\*Column 4, line 17;

"$\{(A)^{\prime}$" should be --$\{(A^{\prime})$--.

Column 5, line 38;

"$n^i+1 \geq 2$" should be --$n^i \geq 2$--.

Column 5, line 39;

"$\geq$ zero" should be --$>$ zero--.

\*Column 9, line 28;

"$\{(A)^{\prime}$" should be --$\{(A^{\prime})$--.

Column 11, line 37;

"$-\{(A^\circ)-(B^\circ)_n oR^\circ$" should be -- $-\{(A^\circ)-(B^\circ)_{no}-R^\circ$--.

\*Column 14, line 51;

"Hydrion$^R$" should be --Hydrion®--.

\*Column 15, line 27;

"azetroped" should be --azeotroped--.

\*Column 15, line 64;

"(90°C" should be --90°C--.

UNITED STATES PATENT AND TRADEMARK OFFICE
CERTIFICATE OF CORRECTION

PATENT NO.   : 5,773,527
DATED        : June 30, 1998
INVENTOR(S)  : Donald A. Tomalia, David M. Hedstrand and Rui Yin Page 2 of 4

It is certified that error appears in the above-identified patent and that said Letters Patent is hereby corrected as shown below:

*Column 16, line 17;

"$^{13}$C NMR" should be --$^{13}$C-NMR--.

*Column 16, line 31;

"$^{13}$C NMR" should be --$^{13}$C-NMR--.

*Column 17, line 62;

"cartride" should be --cartridge--.

*Column 18, line 5;

"form" should be --from--.

*Column 18, line 6;

"is solved" should be --dissolved--.

*Column 18, lines 15 and 45;

"$^{13}$C NMR" should be --$^{13}$C-NMR--.

*Column 18, line 57 and Column 19, line 2;

"$^{13}$C NMR" should be --$^{13}$C-NMR--.

*Column 18, lines 53 and 64;

"sprial" should be --spiral--.

UNITED STATES PATENT AND TRADEMARK OFFICE
CERTIFICATE OF CORRECTION

PATENT NO. : 5,773,527
DATED : June 30, 1998
INVENTOR(S) : Donald A. Tomalia, David M. Hedstrand and Rui Yin It is certified that error appears in the above-identified patent and that said Letters Patent is hereby corrected as shown below:

*Column 19, line 38;

"80 g. 800 mmol)" should be --(80 g. 800 mmol)--.

*Column 19, line 47;

"$^{13}$C NMR" should be --$^{13}$C-NMR--.

*Column 19, line 61;

"separationas" should be --separation as--;

Delete "as", second occurrence.

*Column 20, line 12;

"$^{13}$C NMR" should be --$^{13}$C-NMR--.

*Column 22, line 40;

"$^{13}$C NMR" should be --$^{13}$C-NMR--.

UNITED STATES PATENT AND TRADEMARK OFFICE
CERTIFICATE OF CORRECTION

PATENT NO. : 5,773,527
DATED : June 30, 1998
INVENTOR(S) : Donald A. Tomalia, David M. Hedstrand and Rui Yin It is certified that error appears in the above-identified patent and that said Letters Patent is hereby corrected as shown below:

Column 22, Claim 1, lines 52-63;

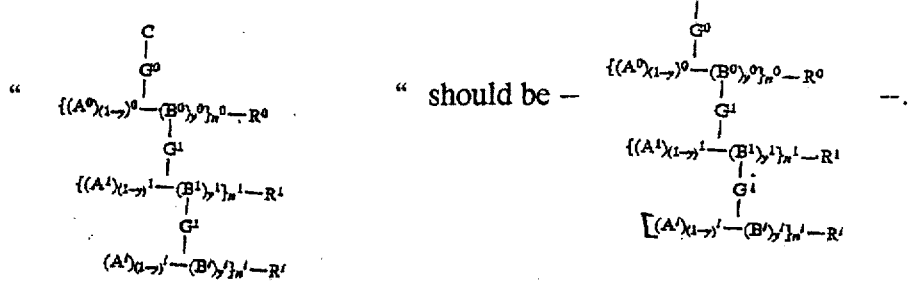

Column 24, Claim 21, line 57;

"(CH2CH2NH-)," should be --(-CH2CH2NH-)--

Signed and Sealed this

Second Day of February, 1999

Attest:

Attesting Officer

Acting Commissioner of Patents and Trademarks